US006814983B2

(12) United States Patent
Giordano et al.

(10) Patent No.: US 6,814,983 B2
(45) Date of Patent: Nov. 9, 2004

(54) COMPOSITIONS AND METHODS FOR NUTRITION SUPPLEMENTATION

(75) Inventors: John A. Giordano, West Orange, NJ (US); Charles Balzer, Lavalette, NJ (US)

(73) Assignee: Everett Laboratories, Inc., West Orange, NJ (US)

(*) Notice: Subject to any disclaimer, the term of this patent is extended or adjusted under 35 U.S.C. 154(b) by 0 days.

(21) Appl. No.: 10/315,159

(22) Filed: Dec. 10, 2002

(65) Prior Publication Data

US 2004/0109901 A1 Jun. 10, 2004

(51) Int. Cl.⁷ .................... A61K 33/24; A61K 31/00
(52) U.S. Cl. .................. 424/630; 424/641; 424/643; 424/646; 424/682; 514/52; 514/167; 514/249; 514/251; 514/276; 514/351; 514/355; 514/458; 514/474; 514/566; 514/567; 514/725; 514/904; 514/905
(58) Field of Search ................... 424/630, 635, 424/641, 643, 646, 648, 682, 686, 692; 514/52, 167, 251, 276, 355, 458, 502, 351, 725, 474, 249, 566, 567, 904, 905

(56) References Cited

U.S. PATENT DOCUMENTS

| | | | |
|---|---|---|---|
| 3,160,564 A | 12/1964 | Hanus | |
| 4,619,829 A | * 10/1986 | Motschan | 424/602 |
| 4,710,387 A | 12/1987 | Uiterwaal et al. | |
| 4,740,373 A | 4/1988 | Kesselman et al. | |
| 4,804,535 A | 2/1989 | Kesselman et al. | |
| 4,940,658 A | 7/1990 | Allen et al. | |
| 4,945,083 A | 7/1990 | Jansen, Jr. | |
| 5,108,767 A | 4/1992 | Mulchandani et al. | |
| 5,278,329 A | 1/1994 | Anderson | |
| 5,374,560 A | 12/1994 | Allen et al. | |
| 5,438,017 A | 8/1995 | Allen et al. | |
| 5,457,055 A | 10/1995 | Allen et al. | |
| 5,494,678 A | 2/1996 | Paradissis et al. | |
| 5,514,382 A | 5/1996 | Sultenfuss | |
| 5,556,644 A | 9/1996 | Chandra | |
| 5,563,126 A | 10/1996 | Allen et al. | |
| 5,626,884 A | 5/1997 | Lockett | |
| 5,795,873 A | 8/1998 | Allen | |
| 5,869,084 A | 2/1999 | Paradissis et al. | |
| 5,898,036 A | 4/1999 | McLeod | |
| 5,922,704 A | 7/1999 | Bland | |
| 5,976,568 A | 11/1999 | Riley | |
| 6,042,849 A | 3/2000 | Richardson et al. | |
| 6,048,846 A | 4/2000 | Cochran | |
| 6,054,128 A | 4/2000 | Wakat | |
| 6,090,414 A | 7/2000 | Passwater et al. | |
| 6,103,756 A | 8/2000 | Gorsek | |
| 6,136,859 A | 10/2000 | Henriksen | |
| 6,207,651 B1 | 3/2001 | Allen et al. | |
| 6,228,388 B1 | 5/2001 | Paradissis et al. | |
| 6,245,360 B1 | 6/2001 | Markowitz | |
| 6,255,341 B1 | 7/2001 | DeMichele et al. | |
| 6,297,224 B1 | 10/2001 | Allen et al. | |
| 6,299,896 B1 | 10/2001 | Cooper et al. | |
| 6,352,713 B1 | * 3/2002 | Kirschner et al. | 424/441 |
| 6,361,800 B1 | 3/2002 | Cooper et al. | |
| 6,451,341 B1 | * 9/2002 | Slaga et al. | 424/468 |
| 6,528,496 B1 | 3/2003 | Allen et al. | |
| 2001/0028896 A1 | 10/2001 | Byrd | |
| 2001/0036500 A1 | 11/2001 | Uchida et al. | |
| 2002/0015742 A1 | 2/2002 | Jackson et al. | |
| 2002/0025310 A1 | 2/2002 | Bland | |
| 2002/0102330 A1 | * 8/2002 | Schramm et al. | 426/72 |

FOREIGN PATENT DOCUMENTS

| | | |
|---|---|---|
| EP | 0 482 715 A1 | 4/1992 |
| EP | 0 891 719 A1 | 1/1999 |
| WO | WO 99/07419 A1 | 2/1999 |

OTHER PUBLICATIONS

Vitafol®–PN product insert, Apr. 1997.
Viitafol® product insert, Jul. 1997.
Vitafol® Syrup product label, 1997.
Stein et al., 3 Blood Purification 52–62 (1985).
Blumberg et al., 20(5) Clin. Nephrol. 244–50 (1983).
Allman et al., 150 Med. J. Australia 130–33 (1999).
Story et al., 27(1) Crit. Care Med. 220–23 (1999).
Makoff, 25 Miner. Electrolyte Metab. 349–51 (1999).
Shah et al., 18(1) Amer. J. Kidney Dis. 84–90 (1991).
Shah et al., 10(1) Amer. J. Kidney Dis. 42–49 (1992).
Vos, 161 Arch. Intern. Med. 774–75 (2001).
House et al., 45(1) Asaio J. 94–97 (1999).
Descombes et al., 24(10) Artificial Organs 773–78 (2000).
The Vitatops Trial Study Group, 13 Cerebrovasc. Dis. 120–126 (2002).
Frank et al., 70(4) Int. J. Vitam. Nutr. Res. 159–66 (2000).
Dierkes et al., 11(2) J. Renal Nutr. 67–72 (2001).
Henning et al., 95(9) Medizin. Klinik 477–81 (2000).
Bazzarre et al., 12(2) J. Amer. Coll. Nutr. 162–69 (1993).
Gey, 52 Bibl. Nutr. Dieta. 75–91 (1995).
Black, 85 Brit. J. Nutr.S193–S197 (2001).
Bostom et al., 49 Kidney Int. 147–152 (1996).
Chang et al., 51 Amer. J. Clin. Nutr. 826–31 (1990).
Moser–Veillon et al., 52 Amer. J. Clin. Nutr. 135–41 (1990).
Kang–Yoon et al., 56 Amer. J. Clin. Nutr. 548–58 (1992).
Christian et al., 130(11) J. Nutr. 2675–82 (2000).
Chelated Materials available a http://www.paws4us.com/minerals.html, (2001).
Lapido, 72 Amer. J. Clin. Nutr. 280S–290S (2002).
Scholl et al., 146 Amer. J. Epidem. 134–141 (1997).
Zile et al., 131 (3) J. Nutr. 705–708 (2001).
Mayne, 10 FASEB Journal 690–701 (1996).

(List continued on next page.)

*Primary Examiner*—Thurman K. Page
*Assistant Examiner*—Frank Choi
(74) *Attorney, Agent, or Firm*—Preston Gates Ellis & Rouvelas Meeds LLP

(57) ABSTRACT

The present invention relates to compositions comprising various vitamins and minerals and methods for using these compositions for nutritional supplementation in, for example, pregnant or lactating subjects.

4 Claims, No Drawings

OTHER PUBLICATIONS

Dawson–Hughes et al, New Eng. J. of Medicine 670–676 (1997).
Lips et al., J. of Clin. Endocrinol. Metab. 1212–21 (2001).
Rock et al., 96(7) J. of Amer. Diet Assoc. 693–702 (1996).
Woods et al., 185(1) Amer. J Obstet. Gynecol. 5–10 (2001).
Kharb, 1 Euro. J. Obstet. Gynecol. Reprod. Biol. 37–39, (2000).
Milczarek et al., 210 Mol. Cell. Biochem. 65–73 (2000).
National Research Council 10$^{th}$ ed. 115–173 (1989).
Stampfer, 328 New Eng. J. Med. 1444–1449 (1993).
Vanderput et al., Exp. Biol. Med. 243–70 (2001).
Defalco, et al., 27 Clin. Exp. Obstet Gynecol. 188–190 (2000).
Eskes, 27 Clin Exp Obstet Gynecol. 157–167 (2000).
Locksmith et al., 91 Obstet. Gynecol. 1027–34 (1998).
Robinson et al., 94 Circulation 2743–2748 (1996).
Henkin et al., 91 Amer. J. Med. 239–246 (1991).
Bothwell, 72 Amer. J. Clin. Nutr. 257S–64S (2000).
Sifakis et al., 900 Ann. N.Y. Acad. Sci. 125–136 (2000).
Groff et al., Advanced Nutrition and Human Metabolism 341 (1995 2$^{nd}$ edition).
Agus et al., 17 Critical Care Clinics 175–187 (2001).
Shecter et al., 102 J. of Am. Heart Assoc. 2353–2358 (2000).
Zima et al., 17 Blood Purif. 182–186 (1999).
Srinivas et al., 68 Indian J of Pediatrics 519–522 (2001).
Yang et al., 13 Biomed Environ Sci. 280–286 (2000).
King, 71 Amer. J. Clin. Nutr. 1334S–1343S (2000).
Uauy et al., 67 Amer. J Clin. Nutr. 952S–959S (1998).
Weigel et al., 12 Controlled Clinical Trials 378–394 (1991).
www.cdc.gov Preventing Neural Tube Birth Defects (2003).

* cited by examiner

COMPOSITIONS AND METHODS FOR NUTRITION SUPPLEMENTATION

FIELD OF THE INVENTION

The present invention relates to compositions comprising various vitamins and minerals and methods for using these compositions for nutritional supplementation in, for example, subjects in physiologically stressful states.

BACKGROUND OF THE INVENTION

Nutrition plays a critical role in maintaining good health. Proper nutrition prevents dietary deficiencies, and also protects against the development of disease. Proper nutrition plays an increasingly important role as the body faces physiological stress. For example, pregnancy and lactation are among the most nutritionally volatile and physiologically stressful periods and processes in the lifetimes of women. Specifically, vitamin and mineral needs are almost universally increased during these natural processes. These increased needs are almost always due to elevated metabolic demand, increased plasma volume, increased levels of blood cells, decreased concentrations of nutrients, and decreased concentrations of nutrient-binding proteins.

Thus, nutritional supplementation serves a vital role in protecting against poor nutrition and disease. More specifically, research has suggested that optimizing specific nutrients before, during, and after the physiological processes of pregnancy or lactation can have a profound, positive, and comprehensive impact upon the overall wellness of the developing and newborn child as well as the safety and health of the mother. The present inventions provide compositions and methods designed to supplement the nutritional needs of individuals within physiologically stressful states.

SUMMARY OF THE INVENTION

The present invention provides compositions and methods of using these compositions for both prophylactic and therapeutic nutritional supplementation, specifically throughout physiologically stressful states.

Specifically, for example, the present invention relates to novel compositions of vitamins and minerals that can be used to supplement the nutritional deficiencies observed in patients throughout physiologically stressful states such as, for example, pregnancy, lactation, and any disease state.

In one embodiment, the compositions of the present invention may comprise less than about 160 mg calcium, more than about 20 mg iron, and copper in either chelated or non-chelated form.

In another embodiment, the compositions of the present invention may comprise one or more of about 2430 IU to about 2970 IU of Vitamin A, about 360 IU to about 440 IU of Vitamin D, about 63 mg to about 77 mg of Vitamin C, about 27 IU to about 33 IU of Vitamin E, about 0.9 mg to about 1.1 mg of folic acid, about 1.44 mg to about 1.76 mg of Vitamin $B_1$, about 1.62 mg to about 1.98 mg of Vitamin $B_2$, about 2.25 mg to about 2.75 mg of Vitamin $B_6$, about 10.8 mcg to about 13.2 mcg of Vitamin $B_{12}$, about 16.2 mg to about 19.8 mg of niacin, about 90 mg to about 110 mg of calcium, about 58.5 mg to about 71.5 mg of iron, about 22.5 mg to about 27.5 mg of magnesium, about 22.5 mg to about 27.5 mg of zinc, and about 1.8 mg to about 2.2 mg of copper.

In yet another embodiment, the compositions of the present invention may comprise one or more of 2700 IU of Vitamin A, 400 IU of Vitamin D, 70 mg of Vitamin C, 30 IU of Vitamin E, 1 mg of folic acid, 1.6 mg of Vitamin $B_1$, 1.8 mg of Vitamin $B_2$, 2.5 mg of Vitamin $B_6$, 12 mcg of Vitamin $B_{12}$, 18 mg of niacin, 100 mg of calcium, 65 mg of iron, 25 mg of magnesium, 25 mg of zinc, and 2 mg of copper.

In an embodiment, the compositions of the present invention may be suitable for administration to subjects in physiologically stressful states. Such compositions may be suitable for treating nutritional deficiencies resulting from such physiologically stressful states, which may result from, for example, elevated metabolic demand, increased plasma volume, or decreased concentrations of nutrient-binding proteins such as serum-ferritin, maltose-binding protein, lactoferrin, calmodulin, tocopheryl binding protein, riboflavin binding protein, retinol binding protein, transthyretin, high density lipoprotein-apolipoprotein A1, folic acid binding protein, and 25-hydroxyvitamin D binding protein. The compositions of the present invention may comprise one or more compounds that serve as pharmaceutical carriers such as water, oil, alcohol, any flavoring agent, any preservative, any coloring agent, starch, any sugar, any diluent, any granulating agent, any lubricant, any binder, and any disintegrating agent.

In one embodiment, the compositions of the present invention may comprise one or more of Vitamin A in the form of beta carotene, Vitamin D in the form of cholecalciferol, Vitamin C in the form of ascorbic acid, Vitamin E in the form of dl-alpha-tocopheryl acetate, a B-complex vitamin in the form of folic acid, Vitamin $B_1$ in the form of thiamine mononitrate, Vitamin $B_2$ in the form of riboflavin, Vitamin $B_6$ in the form of pyridoxine hydrochloride, Vitamin $B_{12}$ in the form of cyanocobalamin, niacin in the form of niacinamide, calcium in the form of calcium carbonate, iron in the form of ferrous fumarate, magnesium in the form of magnesium oxide, zinc in the form of zinc oxide, and/or copper in the form of copper oxide.

The present invention also relates to methods for supplementing nutritional deficiencies in a patient or person throughout physiologically stressful states such as, for example, pregnancy, lactation, and any disease state.

In an embodiment, the methods of the present invention may comprise the step of administering to a patient a composition comprising less than about 160 mg calcium, more than about 20 mg iron, and copper in either chelated or non-chelated form.

In another embodiment, the methods of the present invention may utilize compositions comprising one or more of about 2430 IU to about 2970 IU of Vitamin A, about 360 IU to about 440 IU of Vitamin D, about 63 mg to about 77 mg of Vitamin C, about 27 IU to about 33 IU of Vitamin E, about 0.9 mg to about 1.1 mg of folic acid, about 1.44 mg to about 1.76 mg of Vitamin $B_1$, about 1.62 mg to about 1.98 mg of Vitamin $B_2$, about 2.25 mg to about 2.75 mg of Vitamin $B_6$, about 10.8 mcg to about 13.2 mcg of Vitamin $B_{12}$, about 16.2 mg to about 19.8 mg of niacin, about 90 mg to about 110 mg of calcium, about 58.5 mg to about 71.5 mg of iron, about 22.5 mg to about 27.5 mg of magnesium, about 22.5 mg to about 27.5 mg of zinc, and about 1.8 mg to about 2.2 mg of copper.

In yet another embodiment, the methods of the present invention may utilize compositions comprising one or more of 2700 IU of Vitamin A, 400 IU of Vitamin D, 70 mg of Vitamin C, 30 IU of Vitamin E, 1 mg of folic acid, 1.6 mg of Vitamin $B_1$, 1.8 mg of Vitamin $B_2$, 2.5 mg of Vitamin $B_6$, 12 mcg of Vitamin B12, 18 mg of niacin, 100 mg of calcium, 65 mg of iron, 25 mg of magnesium, 25 mg of zinc, and 2 mg of copper.

In an embodiment, the methods of the present invention utilize the compositions of the present invention suitable for administration to subjects in physiologically stressful states. The methods of the present invention may be directed to the alleviation of nutritional deficiencies resulting from such physiologically stressful states, which may result from, for example, elevated metabolic demand, increased plasma volume, or decreased concentrations of nutrient-binding proteins such as serum-ferritin, maltose-binding protein, lactoferrin, calmodulin, tocopheryl binding protein, riboflavin binding protein, retinol binding protein, transthyretin, high density lipoprotein-apolipoprotein A1, folic acid binding protein, and 25-hydroxyvitamin D binding protein. The methods of the present invention may utilize one or more compounds that serve as pharmaceutical carriers such as water, oil, alcohol, any flavoring agent, any preservative, any coloring agent, starch, any sugar, any diluent, any granulating agent, any lubricant, any binder, and any disintegrating agent.

In one embodiment, the methods of the present invention may utilize compositions comprising one or more of Vitamin A in the form of beta carotene, Vitamin D in the form of cholecalciferol, Vitamin C in the form of ascorbic acid, Vitamin E in the form of dl-alpha-tocopheryl acetate, a B-complex vitamin in the form of folic acid, Vitamin $B_1$ in the form of thiamine mononitrate, Vitamin $B_2$ in the form of riboflavin, Vitamin $B_6$ in the form of pyridoxine hydrochloride, Vitamin B12 in the form of cyanocobalamin, niacin in the form of niacinamide, calcium in the form of calcium carbonate, iron in the form of ferrous fumarate, magnesium in the form of magnesium oxide, zinc in the form of zinc oxide, and/or copper in the form of copper oxide.

Other objectives, features and advantages of the present invention will become apparent from the following detailed description. The detailed description and the specific examples, although indicating specific embodiments of the invention, are provided by way of illustration only. Accordingly, the present invention also includes those various changes and modifications within the spirit and scope of the invention that may become apparent to those skilled in the art from this detailed description.

DETAILED DESCRIPTION OF THE INVENTION

It is understood that the present invention is not limited to the particular methodologies, protocols, solvents, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a vitamin" is a reference to one or more vitamins and includes equivalents thereof known to those skilled in the art and so forth.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the present invention. All references cited herein are incorporated by reference herein in their entirety.

The term "disease state" as used herein, may comprise any state in which one or more organs or components of an organism malfunction. The term "disease state" may refer to any deterioration of any component of a body. The term "disease state" may refer to any deficiency of any compound necessary for the maintenance or function of any component of any organism. The term "disease state" may refer to any condition in which a body contains toxins, produced by microorganisms that infect the body or by body cells through faulty metabolism or absorbed from an external source. "Disease states" may be adverse states caused by any diet, any virus, or any bacteria. "Disease states" may comprise disorders associated with pregnant females such as, for example, osteomalacia and preeclampsia and disorders associated with a fetus such as, for example, neural tube defects and various fetal abnormalities. "Disease states" may comprise any pulmonary disorder such as, for example, bronchitis, bronchiectasis, atelectasis, pneunomia, diseases caused by inorganic dusts, diseases caused by organic dusts, any pulmonary fibrosis, and pleurisy. "Disease states" may comprise any hematological/oncological disorder such as, for example, anemia, hemophilia, leukemia, and lymphoma. A "disease state" may comprise any cancer such as, for example, breast cancer, lung cancer, prostate cancer, pancreatic cancer, liver cancer, stomach cancer, testicular cancer, ovarian cancer, skin cancer, cancer of the brain, cancer of the mouth, cancer of the throat, and cancer of the neck "Disease states" may comprise any disorder of the immune system such as, for example, acquired immune deficiency syndrome (AIDS), AIDS-related complex, infection by any strain of any human immunodeficiency virus (HIV), and other viruses or pathogens such as bacteria. A "disease state" may comprise any cardiovascular disorder such as, for example, arterial hypertension, orthostatic hypotension, arteriosclerosis, coronary artery disease, cardiomyopathy, any arrhythmia, any valvular heart disease, endocarditis, pericardial disease, any cardiac tumor, any aneurysm, and any peripheral vascular disorder. "Disease states" may comprise any hepatic/biliary disorder such as, for example, jaundice, hepatic steatosis, fibrosis, cirrhosis, hepatitis, any hepatic granuloma, any liver tumor, cholelithiasis, cholecystitis, and choledocholithiasis.

The term "physiologically stressful state," as used herein, comprises any state of an organism in which the organism faces one or more physiological challenges. A "physiologically stressful state" may comprise pregnancy, lactation, or conditions in which an organism faces physiological challenges related to, for example, elevated metabolic demand, increased plasma volume, or decreased concentrations of nutrient-binding proteins. A "physiologically stressful state" may result from one or more disease states.

The term "subject," as used herein, comprises any and all organisms and includes the term "patient." "Subject" may refer to a human or any other animal. "Subject" may also refer to a fetus.

Proper nutrition is essential for maintaining health and preventing diseases. Adequate nutrition is especially critical during, for example, nutritionally volatile or physiologically stressful periods such as periods comprising, for example, pregnancy, lactation, or a disease state. Vitamin and mineral needs are almost universally increased throughout these periods. Increased needs during physiologically stressful states such as pregnancy or lactation, for example, may result from elevated metabolic demand, increased plasma volume, increased quantities of circulating red blood cells, decreased concentrations of nutrients, and decreased concentrations of nutrient-binding proteins such as, for example, serum-ferritin, maltose-binding protein, lactoferrin, calmodulin, tocopheryl binding protein, riboflavin binding protein, retinol binding protein, transthyretin, high density lipoprotein-apolipoprotein A1, folic acid binding protein, and 25-hydroxyvitamin D binding protein. Lapido, 72(Supp.) Amer. J. Clin. Nutr. 280S–90S (2000).

Optimizing specific nutrients before, during, and after the physiological processes of pregnancy and lactation can have a profound, positive, and comprehensive impact on the overall wellness of the developing and newborn child as well as the safety and health of the mother. Black, 85 Brit. J. Nutr. S93–97 (Supp. 2001); Scholl et al., 146 Amer. J. Epidem. 134–41 (1997). Nutrients provided to a mother reach the fetus. Specifically, it is established that substrates for growth and development, for example, circulate within the same pathways that carry drugs to and waste products from the fetus. Exchanges of material between mother and fetus occur primarily in the placenta, where villi containing fetal capillaries protrude into sinuses (intervillous spaces). Maternal arterial blood spurts into these spaces, then drains into maternal uterine veins to be returned to the maternal systemic circulation. Solutes in maternal blood cross the epithelial cells and connective tissue of the villi and the endothelium of the fetal capillaries; these solutes are then carried to the fetus by placental veins, which converge into the umbilical vein. The Merck Manual of Diagnosis and Therapy 2022 (Mark H. Beers, M.D. & Robert Berkow, M.D. eds., 17th ed. 1999).

The compositions and methods of the present invention provide the means to optimize good health by utilizing vitamin and mineral nutritional supplementation. The compositions and methods of the present invention may be administered to or directed to a subject such as a human or any other organism.

The compositions and methods of the present invention may comprise or use Vitamin A. This vitamin functions in physiological processes resulting in cellular differentiation, cellular maturity, and cellular specificity. Vitamin A is an important component of a nutritional supplement for subjects in a physiologically stressful state, such as pregnant or lactating women. Zile et al., 131(3) J. Nutr. 705–08 (2001). The compounds and methods of the present invention may comprise a form of Vitamin A, specifically, for example, the pro-vitamin A carotenoid beta carotene. Beta carotene is converted to Vitamin A within the body as needed. Mayne, 10 Faseb J. 690–701 (1996). The novel compositions and methods of the present invention may comprise or use Vitamin A, specifically in amounts ranging from about 2430 IU to about 2970 IU and, in a specific embodiment, around 2700 IU.

The compositions and methods of the present invention may comprise or use Vitamin D. Vitamin D is a fat-soluble "hormone like" substance important for the maintenance of healthy bones. This vitamin increases the absorption of calcium and phosphorous from the gastrointestinal tract, and improves mineral resorption into bone tissue. Vitamin D can be converted to its active form from exposure of the skin to sunlight. This fact is among the reasons why Vitamin D deficiency is common in the elderly, notably the institutionalized, who spend little or no time out of doors. Deficiencies lead to increased bone turnover and loss, and when severe, osteomalacia, or softening of the bones. Supplementation with Vitamin D has been shown to moderately reduce bone loss, increase serum 25-hydroxyvitamin D, and decrease serum parathyroid hormone levels. Dawson-Hughes et al., 337 New Eng. J. Med. 670–76 (1997); Lips et al., 86 J. Clin. Endocrinol. Metab. 1212–21 (2001).

The Vitamin D of the compositions and methods of the present invention may comprise Vitamin $D_3$ (cholecalciferol). In the body, Vitamin $D_3$ is produced when its precursor is exposed to ultraviolet irradiation (e.g., sunlight) and then hydroxylated in the liver to form 25-hydroxyvitamin $D_3$, a form of Vitamin D in circulation. This form of the vitamin may be hydroxylated again in the kidney, yielding 1,25-hydroxyvitamin $D_3$, a potent form of Vitamin D. Vitamin $D_3$ plays a role in the maintenance of calcium and phosphorus homeostasis, but it is also active in cell differentiation and immune function. The novel compositions and methods of the present invention may comprise or use Vitamin D, specifically in amounts ranging from about 360 IU to about 440 IU and, in a specific embodiment, around 400 IU.

The compositions and methods of the present invention may comprise or use Vitamin C (also known as ascorbic acid). The major biochemical role of the water-soluble Vitamin C is as a co-substrate in metal catalyzed hydroxylations. Vitamin C has antioxidant properties in interacting directly with superoxide hydroxyl radicals and singlet oxygen. Vitamin C also provides antioxidant protection for folate and Vitamin E, keeping Vitamin E in its most potent form.

Lipid peroxidation has been associated with over 200 disease processes. Rock et al., 96(7) J. Amer. Diet. Assoc. 693–702 (1996). Specifically, lipid peroxidation may be implicated, for example, in the pathophysiology of preeclampsia, a toxemia of pregnancy. Vitamin C may afford protective effects against preeclampsia by participating in the scavenging of free radicals. Indeed, significantly lower levels of Vitamin C have been observed in preeclamptic women than in controls. Woods et al., 185(1) Am. J. Obstet. Gynecol. 5–10 (2001); Kharb, 1 Euro. J. Obstet. Gynecol. Reprod. Biol. 37–39 (2000); Milczarek et al., 210 Mol. Cell. Biochem. 65–73 (2000).

Vitamin C also enhances the absorption of iron. National Research Council, Recommended Dietary Allowances 115 (10th ed. 1989) (hereinafter "RDA"). In addition, Vitamin C is required for collagen synthesis, epinephrine synthesis, and bile acid formation. Moreover, Vitamin C has been implicated in inhibiting atherosclerosis by being present in extracellular fluid of the arterial wall and potentiating nitric oxide activity, thus normalizing vascular function. The novel compositions and methods of the present invention may comprise or use Vitamin C, specifically in amounts ranging from about 63 mg to about 77 mg and, in a specific embodiment, around 70 mg.

The compositions and methods of the present invention may comprise or use Vitamin E. Vitamin E is a fat-soluble vitamin antioxidant found in biological membranes where it protects the phospholipid membrane from oxidative stress. One form of Vitamin E, dl-alpha-tocopheryl acetate (BASF Corporation, Mount Olive, N.J.), is used to fortify foods and pharmaceuticals and may be used within the context of the present invention. Vitamin E inhibits the oxidation of unsaturated fatty acids by trapping peroxyl free radicals. It is also an antiatherogenic agent, and studies have demonstrated a reduced risk of coronary heart disease with increased intake of Vitamin E. Stampfer et al., 328 New Eng. J. Med. 1444–49 (1993). In addition, Vitamin E, like Vitamin C, may afford protective effects against preeclampsia by participating in the scavenging of free radicals. Indeed, significantly lower levels of Vitamin E have been observed in preeclamptic women than in controls. Woods et al., 185(1) Am. J. Obstet. Gynecol. 5–10 (2001); Kharb, 1 Euro. J. Obstet. Gynecol. Reprod. Biol. 37–39 (2000); Milczarek et al., 210

Mol. Cell. Biochem. 65–73 (2000). The novel compositions and methods of the present invention may comprise or use Vitamin E, specifically in amounts ranging from about 27 IU to about 33 IU and, in a specific embodiment, around 30 IU.

The compositions and methods of the present invention may comprise or use B-complex vitamins. This class of vitamins comprises the water-soluble nutrients not generally stored in the body. The B-complex vitamins of the present compositions and methods may comprise one or more of thiamine ($B_1$), riboflavin ($B_2$), niacin ($B_3$), folic acid, pyridoxine ($B_6$) and cyanocobalamin ($B_{12}$). B-complex vitamins play roles in a variety of biological processes critical to the health of pregnant women, lactating women, and fetuses such as, for example, the metabolism of homocysteine.

The compositions and methods of the present invention may comprise or use folic acid. The B-complex vitamin folic acid has demonstrated the ability to prevent neural tube defects such as spina bifida caused by disturbed homocysteine metabolism. Vanderput et al., Exp. Biol. Med. 243–70 (2001); DeFalco et al., 27 Clin. Exp. Obstet. Gynecol. 188–90 (2000); Eskes, 27 Clin. Exp. Obstet. Gynecol. 157–67 (2000); Locksmith & Duff, 91 Obstet. Gynecol. 1027–34 (1998). Further, folic acid is important for the formation of red and white blood cells within bone marrow and plays a role in heme formation. RDA at 150. The novel compositions and methods of the present invention may comprise or use folic acid, specifically in amounts ranging from about 0.9 mg to about 1.1 mg and, in a specific embodiment, around 1.0 mg.

The compositions and methods of the present invention may comprise or use Vitamin $B_1$. This vitamin plays a role in carbohydrate metabolism and neural function. It is a coenzyme for the oxidative decarboxylation of alpha-ketoacids (e.g., alpha-ketoglutarate and pyruvate) and for transketolase which is a component of the pentose phosphate pathway. Folate deficiency and malnutrition inhibit the activity of thiamine. RDA at 123. Vitamin $B_1$ is available in forms known to those of skill in the art, including the form of thiamine mononitrate (BASF Corporation, Mount Olive, N.J.). The novel compositions and methods of the present invention may comprise or use Vitamin $B_1$, specifically in amounts ranging from about 1.44 mg to about 1.76 mg and, in a specific embodiment, around 1.6 mg.

The compositions and methods of the present invention may comprise or use Vitamin $B_2$ (riboflavin). Riboflavin is a component of two flavin coenzymes, flavin mononucleotide (FMN) and flavin adenine dinucleotide (FAD). These flavoenzymes are involved in a number of oxidation-reduction reactions including the conversion of pyridoxine and niacin. RDA at 132. Flavoenzymes also play a role in a number of metabolic pathways such as amino acid deamination, purine degradation, and fatty acid oxidation and thus help to maintain carbohydrate, amino acid, and lipid metabolism. The novel compositions and methods of the present invention may comprise or use Vitamin $B_2$, specifically in amounts ranging from about 1.62 mg to about 1.98 mg and, in a specific embodiment, around 1.8 mg.

The compositions and methods of the present invention may comprise or use Vitamin $B_6$ (pyridoxine). The administration of pyridoxine may reduce the levels of homocysteine. Bostom et al., 49 Kidney Int. 147–52 (1996). The active forms of pyridoxine, pyridoxal-5'-phosphate (PLP) and pyridoxamine-5'-phosphate are coenzymes for numerous enzymes and as such, are important for gluconeogenesis, niacin formation, and erythrocyte metabolism. RDA at 142–43. Pyridoxine is a coenzyme for both cystathionine synthase and cystathionase, enzymes that catalyze the formation of cysteine from methionine. Homocysteine is an intermediate in this process and elevated levels of plasma homocysteine are recognized as a risk factor for both vascular disease (Robinson et al., 94 Circulation 2743–48 (1996)) and neural tube defects (Locksmith & Duff, 91 Obstet. Gynecol. 1027–34 (1998)). Vitamin $B_6$ is available in forms known to those of skill in the art, including the form of pyridoxine hydrochloride (BASF Corporation, Mount Olive, N.J.). The novel compositions and methods of the present invention may comprise or use Vitamin $B_6$, specifically in amounts ranging from about 2.25 mg to about 2.75 mg and, in a specific embodiment, around 2.5 mg.

The compositions and methods of the present invention may comprise or use Vitamin $B_{12}$. Cobalamin (a form of Vitamin $B_{12}$) can be converted to the active coenzymes, methylcobalamin and 5'-deoxyadenosylcobalamin. These coenzymes are necessary for folic acid metabolism, conversion of coenzyme A, and myelin synthesis. For example, methylcobalamin catalyzes the demethylation of a folate cofactor which is involved in DNA synthesis. A lack of demethylation may result in folic acid deficiency. RDA at 159–60. Deoxyadenosylcobalamin is the coenzyme for the conversion of methylmalonyl-CoA to succinyl-CoA, which plays a role in the citric acid cycle. Importantly, cobalamin, along with pyridoxine and folic acid in implicated in the proper metabolism of homocysteine. Cobalamin is available as cyanocobalamin, methylcobalamin, hydroxocobalamin, adenosylcobalamin, and hydroxycyanocobalamin. The novel compositions and methods of the present invention may comprise or use Vitamin $B_{12}$, specifically in amounts ranging from about 10.8 mcg to about 13.2 mcg and, in a specific embodiment, around 12 mcg.

The compositions and methods of the present invention may comprise or use niacin. Niacin, also called Vitamin $B_3$, is the common name for two compounds: nicotinic acid (also called niacin) and niacinamide (also called nicotinamide). Niacin is particularly important for maintaining healthy levels and types of fatty acids. Niacin is also required for the synthesis of pyroxidine, riboflavin, and folic acid. RDA at 137. Administration of niacin may also effect a reduction in total cholesterol (LDL) and very low density lipoprotein (VLDL) levels and an increase in high density lipoprotein (HDL) cholesterol levels. Nicotinamide adenine dinucleotide (NAD) and NAD phosphate (NADP) are active coenzymes of niacin. These coenzymes are involved in numerous enzymatic reactions such as glycolysis, fatty acid metabolism, and steroid synthesis. Henkin et al., 91 Am. J. Med. 239–46 (1991). The novel compositions and methods of the present invention may comprise or use niacin, specifically in amounts ranging from about 16.2 mg to about 19.8 mg and, in a specific embodiment, around 18 mg.

Minerals are inorganic, or non-carbon-containing, elements that are critical for healthy physiological processes. Minerals are contemplated in the compositions and methods of the present invention. Such minerals may be in either chelated or non-chelated form. For example, minerals act as cofactors for hundreds of enzymes associated, for example, with food digestion, nucleic acid production, and protein synthesis. Minerals may also act as, for example, cofactors for antioxidant enzymes. The minerals of the compositions and methods of the present invention may comprise one or more of calcium, iron, magnesium, zinc, and copper.

The compositions and methods of the present invention may comprise or use calcium in either chelated or non-chelated form. Chelation of calcium may affect its bioavailability. Chelated Minerals, available at http:// www.paws4us.com/minerals.html (last visited 8 Nov. 2002). This mineral is required for proper functioning of numerous intracellular and extracellular processes including, for example, muscle contraction, nerve conduction, blood coagulation, and of particular interest in the context of pregnancy and lactation, hormone release. In addition, the calcium ion plays a unique role in intracellular signaling and is involved in the regulation of many enzymes. The Merck Manual of Diagnosis and Therapy 139 (Mark H. Beers, M.D. & Robert Berkow, M.D. eds., 17th ed. 1999). Calcium is available in forms known to those of skill in the art, including the form of calcium carbonate, the active ingredient in TUMS® (GlaxoSmithKline, Research Triangle Park, N.C.). The novel compositions and methods of the present invention may comprise or use calcium, specifically in amounts ranging from about 90 mg to about 110 mg and, in a specific embodiment, around 100 mg. Further, the novel compositions and methods of the present invention may comprise or use calcium in amounts less than about 160 mg. In addition, the novel compositions and methods of the present invention may comprise or use calcium in amounts ranging from about 0.001 mg to about 160 mg. In addition, the novel compositions and methods of the present invention may comprise or use calcium in amounts of 0 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, or 160 mg.

The compositions and methods of the present invention may comprise or use iron in either chelated or non-chelated form. Chelation of iron may affect its bioavailability. Chelated Minerals, available at http://www.paws4us.com/minerals.html (last visited 8 Nov. 2002). A primary function of iron is to carry oxygen to bodily tissues via the hemoglobin part of red blood cells. Supplemental intake of iron is critical to preventing anemia, a disorder associated with a variety of physiological states including, for example, pregnancy. Bothwell, 72(Supp.) Am. J. Clin. Nutr. 257S–64S (2000). Severe anemia may have adverse effects upon a mother and a fetus. Specifically, significant depression of hemoglobin has been associated with poor pregnancy outcome. Black, 85(Supp. 2) Brit. J. Nutr. S193–97 (2001); Sifakis & Pharmakides, 900 Ann. N.Y. Acad. Sci. 125–36 (2000). One form of iron known in the art is ferrous fumarate (Jost Chemical, St. Louis, Mo.). The novel compositions and methods of the present invention may comprise or use iron, specifically in amounts ranging from about 58.5 mg to about 71.5 mg and, in a specific embodiment, around 65 mg. In addition, the novel compositions and methods of the present invention may comprise or use iron in amounts more than about 20 mg. In addition, the novel compositions and methods of the present invention may comprise or use iron in amounts of 0 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, or 80 mg.

The compositions and methods of the present invention may comprise or use magnesium in either chelated or nonchelated form. Chelation of magnesium may affect its bioavailability. Chelated Minerals, available at http://www.paws4us.com/minerals.html (last visited 8 Nov. 2002). Magnesium is important for over 300 different enzyme reactions. A primary function of magnesium is to bind to phosphate groups in adenosine triphosphate (ATP), thereby forming a complex that assists in the transfer of ATP phosphate. Magnesium also functions within cells as an allosteric activator of enzyme activity and for membrane stabilization. Magnesium also plays roles in nucleic acid synthesis, transcription of DNA and RNA, amino acid activation, and protein synthesis. James L. L. Groff et al., Advanced Nutrition and Human Metabolism 341 (2d ed. 1996).

Magnesium is found primarily in both bone and muscle. Magnesium is related to the reactions of over 300 enzymes, including enzymes associated with biosynthetic pathways, glycolysis, protein synthesis, transketolase reactions, and membrane transport. Magnesium is also involved in the formation of cAMP, a cytosolic second messenger that plays a role in cell signaling mechanisms. In addition, magnesium functions both synergistically and antagonistically with calcium in neuromuscular transmission. RDA at 188. Specifically, magnesium is critical for the maintenance of electrochemical potentials of nerve and muscle membranes and the neuromuscular junction transmissions, particularly important in the heart. Not surprisingly, magnesium deficiency is tied to cardiovascular disease and hypertension. Agus et al., 17 Crit. Care Clinics 175–87 (2001). Indeed, oral magnesium therapy improves endothelial function in patients with coronary disease. Shechter et al., 102 Circulation 2353–58 (2000).

Magnesium is available in a variety of salts. One form of magnesium known in the art is magnesium oxide (Mallinckrodt Baker, Inc., Phillipsburg, N.J.). The novel compositions and methods of the present invention may comprise or use magnesium, specifically in amounts ranging from about 22.5 mg to about 27.5 mg and, in a specific embodiment, around 25 mg.

The compositions and methods of the present invention may comprise or use zinc in either chelated or non-chelated form. Chelation of zinc may affect its bioavailability. Chelated Minerals, available at http://www.paws4us.com/minerals.html (last visited 8 Nov. 2002). Zinc plays a role in numerous metabolic activities such as nucleic acid production, protein synthesis, and development of the immune system. There are more than 200 zinc metalloenzymes including aldolase, alcohol dehydrogenase, RNA polymerase, and protein kinase C. Zima et al., 17 Blood Purif. 182–86 (1999). Zinc stabilizes RNA and DNA structures, forms zinc fingers in nuclear receptors, and is a component of chromatin proteins involved in transcription and replication. Deficiencies of zinc during pregnancy have been shown to contribute to severe fetal abnormalities. Srinivas et al., 68(6) Indian J. Pediatr. 519–22 (2001); Yang et al., 13(4) Biomed. Environ. Sci. 280–86 (2000); King, 71(Supp.) Am. J. Clin. Nutr. 1334S–43S (2000). Zinc is available in many forms, such as zinc oxide (Reade Advanced Materials, Providence, R.I.) and zinc sulfate (United States Biological, Swampscott, Mass.). The novel compositions and methods of the present invention may comprise or use zinc, specifically in amounts ranging from about 22.5 mg to about 27.5 mg and, in a specific embodiment, around 25 mg.

The compositions and methods of the present invention may comprise or use copper in either chelated or non-chelated form. Chelation of copper may affect its bioavailability. Chelated Minerals, available at http://www.paws4us.com/minerals.html (last visited 8 Nov. 2002). Copper is an important component of the process of gene expression. Deficiencies of copper may lead to anemia, neutropenia, and bone abnormalities in pregnant and lactating women. In addition, a fetus must accumulate copper at a rate of 50 $\mu g \times kg^{-1} \times d^{-1}$ over the latter half of pregnancy; any deficiency in accumulation may lead to low birth weight and protein-energy malnutrition. Uauy et al., 67(Supp.) Amer. J. Clin. Nutr. 952S–59S (1998). Many forms of copper are known to those skilled in the art, including copper oxide (Reade Advanced Materials, Providence, R.I.). The novel compositions and methods of the present invention may comprise or use copper, specifically in amounts ranging from about 1.8 mg to about 2.2 mg and, in a specific embodiment, around 2.0 mg. The novel compositions and methods of the present invention may comprise or use copper, specifically in amounts of 0 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, or 3.0 mg.

The compositions and methods of the present invention may comprise or use a combination of vitamins and minerals, in either chelated or non-chelated form, that work together with various metabolic systems and physiological responses of the human body. The active ingredients are available from numerous commercial sources, and in several active forms or salts thereof, known to those of ordinary skill in the art. Hence, the compositions and methods of the present invention are not limited to comprising or using any particular form of the vitamin or mineral ingredient described herein.

The ingredients of the present invention may be combined into a composition which may be in the form of a solid powder, caplets, tablets, lozenges, pills, capsules, or a liquid, and which may be administered alone or in suitable combination with other components. For example, the composition of the present invention may be administered in one or more caplets or lozenges as practical for ease of administration. Each of the vitamins and minerals is commercially available, and can be blended to form a single composition or can form multiple compositions, which may be co-administered.

To prepare the compositions of the present invention, each of the active ingredients may be combined in intimate admixture with a suitable carrier according to conventional compounding techniques. The carrier may take a wide variety of forms depending upon the form of the preparation desired for administration, e.g., oral, sublingual, nasal, via topical patch, or parenteral. The composition may consist of one to three caplets or lozenges, the composition of each preferably being identical to each other caplet or lozenge.

In preparing the composition in oral dosage form, any usual media may be utilized. For liquid preparations (e.g., suspensions, elixirs, and solutions), media containing, for example water, oils, alcohols, flavoring agents, preservatives, coloring agents and the like may be used. Carriers such as starches, sugars, diluents, granulating agents, lubricants, binders, disintegrating agents and the like may be used to prepare oral solids (e.g., powders, caplets, pills, tablets, capsules, and lozenges). Controlled release forms may also be used. Because of their ease in administration, caplets, tablets, pills, and capsules represent the most advantageous oral dosage unit form, in which case solid carriers are employed. If desired, tablets may be sugar coated or enteric coated by standard techniques. All of these pharmaceutical carriers and formulations are well known to those of ordinary skill in the art. See generally, e.g., Wade & Waller, Handbook of Pharmaceutical Excipients (2nd ed. 1994).

Other objectives, features and advantages of the present invention will become apparent from the following specific examples. The specific examples, while indicating specific embodiments of the invention, are provided by way of illustration only. Accordingly, the present invention also includes those various changes and modifications within the spirit and scope of the invention that may become apparent to those skilled in the art from this detailed description. The invention will be further illustrated by the following non-limiting examples.

EXAMPLES

Without further elaboration, it is believed that one skilled in the art, using the preceding description, can utilize the present invention to the fullest extent. The following examples are illustrative only, and not limiting of the remainder of the disclosure in any way whatsoever.

Example 1

A composition of the following formulation was prepared in caplet form, including the appropriate excipients, by standard methods known to those of ordinary skill in the art:

Vitamin A (beta carotene) 2700 IU

Vitamin D (cholecalciferol) 400 IU

Vitamin C (ascorbic acid) 70 mg

Vitamin E (dl-alpha-tocopheryl acetate) 30 IU folic acid 1.0 mg

Vitamin $B_1$ (thiamine mononitrate) 1.6 mg

Vitamin $B_2$ (riboflavin) 1.8 mg

Vitamin $B_6$ (pyridoxine hydrochloride) 2.5 mg

Vitamin B12 (cyanocobalamin) 12 mcg niacin (niacinamide) 18 mg calcium (calcium carbonate) 100 mg iron (ferrous fumarate) 65 mg magnesium (magnesium oxide) 25 mg zinc (zinc oxide) 25 mg copper (copper oxide) 2.0 mg Example 2

A study is undertaken to evaluate the effectiveness of the composition of the present invention in the treatment of patients. The objective of the study is to determine whether oral intake of the composition results in an improvement of the nutritional status of a patient in a physiologically stressful state.

A double-blind, placebo controlled study is conducted over a six-month period. A total of 120 subjects (60 pregnant women entering the second trimester of pregnancy and 60 lactating women), aged 20–35 years, are chosen for the study. An initial assessment of the nutritional status of each woman is conducted utilizing methods such as the peroxide hemolysis test to assess Vitamin E deficiency, measurement of erythrocyte transketolase activity to determine thiamine levels, determination of erythrocyte glutathione reductase activity to assess riboflavin status, and high performance liquid chromatography to directly measure pyridoxine levels.

The 120 subjects are separated into four separate groups of 30 women. In a first group comprising only pregnant women and in a second group comprising only lactating women, each subject is administered 2 caplets, daily, of the composition as described in Example 1. In a third group comprising only pregnant women and in a fourth group comprising only lactating women, each subject is administered 2 placebo caplets, daily. No other nutritional supplements are taken by the subjects during the assessment period.

An assessment of the nutritional status of each woman is conducted utilizing methods such as the peroxide hemolysis test to assess Vitamin E deficiency, measurement of erythrocyte transketolase activity to determine thiamine levels, determination of erythrocyte glutathione reductase activity to assess riboflavin status, and high performance liquid chromatography to directly measure pyridoxine levels at one month intervals for a six month period. The data is evaluated using multiple linear regression analysis and a standard t-test. In each analysis, the baseline value of the outcome variable is included in the model as a covariant. Treatment by covariant interaction effects is tested by the method outlined by Weigel & Narvaez, 12 Controlled Clinical Trials 378–94 (1991). If there are no significant interaction effects, the interaction terms are removed from the model. The regression model assumptions of normality and homogeneity of variance of residuals are evaluated by inspection of the plots of residuals versus predicted values. Detection of the temporal onset of effects is done sequentially by testing for the presence of significant treatment effects at 1, 2, 3, 4, 5, and 6 months, proceeding to the earlier time in sequence only when significant effects have been identified at each later time period. Changes from the baseline within each group are evaluated using paired t-tests. In addition, analysis of variance is performed on all baseline measurements and measurable subject characteristics to assess homogeneity between groups. All statistical procedures are conducted using the Statistical Analysis System (SAS Institute Inc., Cary, N.C.). An alpha level of 0.05 is used in all statistical tests.

A statistically significant improvement in the nutritional status with respect to Vitamin E, thiamine, riboflavin, and pyridoxine is observed in the treated subjects upon completion of the study over the controls. Therefore, the study confirms that oral administration of the composition of the present invention is effective in improving the nutritional status of a patient within a physiologically stressful state.

While there has been described what is presently believed to be the preferred embodiments of the present invention, other and further modifications and changes may be made without departing from the spirit of the invention. All further and other modifications and changes are included that come within the scope of the invention as set forth in the claims. The disclosure of all publications cited above are expressly incorporated by reference in their entireties to the same extent as if each were incorporated by reference individually.

We claim:

1. A composition comprising about 2430 IU to about 2970 IU Vitamin A, about 360 IU to about 440 IU Vitamin D, about 63 mg to about 77 mg Vitamin C, about 27 IU to about 33 IU Vitamin E, about 0.9 mg to about 1.1 mg folic acid, about 1.44 mg to about 1.76 mg Vitamin B1, about 1.62 mg to about 1.98 mg Vitamin B2, about 2.25 mg to about 2.75 mg Vitamin B6, about 10.8 mcg to about 13.2 mcg Vitamin B12, about 16.2 mg to about 19.8 mg niacin, about 90 mg to about 110 mg calcium, about 58.5 mg to about 71.5 mg iron, about 22.5 mg to about 27.5 mg magnesium, about 22.5 mg to about 27.5 mg zinc, and about 1.8 mg to about 2.2 mg copper, wherein said composition is administerable to a patient, and wherein said composition is free of any other added minerals and any other added vitamins.

2. A composition comprising 2700 IU Vitamin A, 400 IU Vitamin D, 70 mg Vitamin C, 30 IU Vitamin E, 1 mg folic acid, 1.6 mg Vitamin B1, 1.8 mg Vitamin B2, 2.5 mg Vitamin B6, 12 mcg Vitamin B12, 18 mg niacin, 100 mg calcium, 65 mg iron, 25 mg magnesium, 25 mg zinc, and 2 mg copper, wherein said composition is administerable to a patient, and wherein said composition is free of any other added minerals and any other added vitamins.

3. A method comprising the step of administering to a patient a composition comprising about 2430 IU to about 2970 IU Vitamin A, about 360 IU to about 440 IU Vitamin D, about 63 mg to about 77 mg Vitamin C, about 27 IU to about 33 IU Vitamin E, about 0.9 mg to about 1.1 mg folic acid, about 1.44 mg to about 1.76 mg vitamin B1, about 1.62 mg to about 1.98 mg Vitamin B2, about 2.25 mg to about 2.75 mg Vitamin B6, about 10.8 mcg to about 13.2 mcg Vitamin B12, about 16.2 mg to about 19.8 mg niacin, about 90 mg to about 110 mg calcium, about 58.5 mg to about 71.5 mg iron, about 22.5 mg to about 27.5 mg magnesium, about 22.5 mg to about 27.5 mg zinc, and about 1.8 mg to about 2.2 mg copper, wherein said composition is free of any other added minerals and any other added vitamins.

4. A method comprising the step of administering to a patient a composition comprising 2700 IU Vitamin A, 400 IU Vitamin D, 70 mg Vitamin C, 30 IU Vitamin E, 1 mg folic acid, 1.6 mg Vitamin B1, 1.8 mg Vitamin B2, 2.5 mg Vitamin B6, 12 mcg Vitamin B12, 18 mg niacin, 100 mg calcium 65 mg iron, 25 mg magnesium, 25 mg zinc, and 2 mg copper, wherein said composition is free of any other added minerals and any other added vitamins.

* * * * *

UNITED STATES PATENT AND TRADEMARK OFFICE
CERTIFICATE OF CORRECTION

PATENT NO. : 6,814,983 B2
DATED : November 9, 2004
INVENTOR(S) : John A. Giordano et al.

It is certified that error appears in the above-identified patent and that said Letters Patent is hereby corrected as shown below:

Column 14,
Lines 24 and 32, delete "administerable" and insert -- administrable --.

Signed and Sealed this

Fifteenth Day of February, 2005

JON W. DUDAS
*Director of the United States Patent and Trademark Office*